United States Patent [19]

Inaba et al.

[11] Patent Number: 5,219,841
[45] Date of Patent: Jun. 15, 1993

[54] TREATMENT OF ARRHYTHMIA BY ADMINISTRATION OF AP$_4$A

[75] Inventors: Niro Inaba, Hino; Kunihiro Okamura, Musashino; Tetsuaki Yamaura, Niiza, all of Japan

[73] Assignees: Fujirebio, Inc., Tokyo; Unitika Ltd., Hyogo, both of Japan

[21] Appl. No.: 616,028

[22] Filed: Nov. 20, 1990

[30] Foreign Application Priority Data

Nov. 24, 1989 [JP] Japan .................................. 1-306092

[51] Int. Cl.$^5$ ............................................ A61K 31/70
[52] U.S. Cl. ............................... 514/47; 536/26.22
[58] Field of Search ................. 536/26; 514/46–47

[56] References Cited

U.S. PATENT DOCUMENTS 3,321,463  5/1967  Moffatt ............................ 536/27 X

FOREIGN PATENT DOCUMENTS 0247819  12/1987  European Pat. Off. .
8904321   5/1989  World Int. Prop. O. .

OTHER PUBLICATIONS

Busse et al., "Vasomotor Activity of Diadenosine Triphosphate and Diadenosine Tetraphosphate in Isolated Arteries," *Am. J. Physiol.*, 254(5), H828–H832 (1988).
Nees, "Coronary Flow Increases Induced by Adenosine and Adenine Nucleotides Are Mediated by the Coronoray Endothelium: A New Principle of the Regulation of Coronary Flow," *European Heart J.*, 10, Supplement F, 28–35 (1989).
"Martindale, The Extra Pharmacopoeia, 29th Ed.," Reynolds et al. eds., The Pharmaceutical Press, London, 1989, at p. 1492, see entires for AMP (#9201-m) and ATP (#9203-v).
Luthje, J., *Klinisch Wochen-schrift* 67:317–327 (1989).
Luthje et al., *Biochem. Biophys. Res. Comm*, 118(3), 704–709 (1984).
Luthje et al., *Eur. J. Biochem.*, 149, 119–127 (1985).
Blackburn et al., *Nucleic Acids Research*, 15(17), 6991–7004 (1987).
Harrison et al., *FEBS Letters*, 54(1), 57–60 (1975).
Elmaleh et al., *Proc. Natl. Acad. Sci. USA*, 81, 918–921 (1984).
"Metabolism of Diadenosine Tetraphosphate (Ap$_4$A)," Conference Abstracts published in *Hoppe-Seyler's Z. Physiol. Chem.*, 365, S597–611 (1984).
Guranowski et al., *Biochemistry*, 26, 3425–3429 (1987).
Feldhaus et al., *Chem. Abstr.*, 83: 159,849u (1975); see also *Eur. J. Biochem.*, 57(1), 197–204 (1975).
Taurosva et al., *Chem. Abstr.*, 105: 227,203e (1986); see also *Bioorg. Khim.*, 12(3), 404–407 (1986).
Fukunaga et al., *Anesthesia and Analgesia*, 61, 273–278 (1982).

*Primary Examiner*—Johnnie R. Brown
*Assistant Examiner*—L. Eric Crane
*Attorney, Agent, or Firm*—David G. Conlin; Ronald I. Eisenstein

[57] ABSTRACT

The present invention relates to a pharmaceutical composition for treating a heart disease which comprises a therapeutically effective amount of diadenosine 5',5'''-P$^1$, P$^4$-tetraphosphate as an active ingredient in admixture with a pharmaceutically acceptable carrier or diluent. The pharmaceutical composition is particularly characterized by having antiarrhythmic and coronary vasodilative activities. The present invention also relates to a method for treating a subject having a heart disease or particularly arrhythmia, which comprises administering to the subject an effective amount of the pharmaceutical composition.

4 Claims, 6 Drawing Sheets

TREATMENT OF ARRHYTHMIA BY ADMINISTRATION OF AP$_4$A

BACKGROUND OF THE INVENTION

1. Field of the Invention

The present invention relates to a pharmaceutical composition for treating a heart disease which comprises diadenosine 5',5'''-P$^1$, P$^4$-tetraphosphate as an active ingredient and to a method for treating a subject having a heart disease which comprises administering the pharmaceutical composition to the subject. More particularly, it relates to the pharmaceutical composition having antiarrhythmic and coronary vasodilative activities.

2. Description of the Prior Art

There tends to be a gradual increase in morbidity rate for cardiovascular diseases such as heart disease, arteriosclerosis and hypertension, as the number of the aged people increases and western-style dietary life becomes popular. Particularly, mortality from heart disorders ranks next to that from cancer, thus being one of the social problems. Cardiac disorders commonly include arrhythmia, heart failure, angina pectoris, coronary atherosclerosis, myocardial infarction, etc. Drugs for treating these disorders may be classified accordingly into antiarrhythmic agents, cardiotonics, coronary vasodilators, and so forth.

Arrhythmia arises from abnormalities in the rhythm of cardiac beat which should normally proceed at a regular pace, in particular an abnormality in the generation of spontaneous impulse in the sinoatrial node and an abnormality in the conduction system. It is classified into tachyarrhythmia and bradyarrhythmia according to frequency of the rhythm of cardiac beat.

Drugs for treatment of arrhythmia include the following groups: sodium ion channel inhibitors which exert an antirrhythmic effect by inhibiting the conduction system in the His bundle, Purkinje fibers, atrium, or ventricular muscle, through an electrophysiological mechanism; β-blockers which indirectly inhibit the calcium ion channels in myocardial cell membranes, thus being effective in a treatment of the arrhythmia which arises from sympathicotonia or of the supraventricular arrhythmia in which the sinoatrial node and/or the atrioventricular node take part; drugs which exert an antiarrhythmic effect by prolonging a duration of action potential in all myocardial cells with the associated prolongation of refractory period and without the inhibition of sodium ion channel; calcium antagonists which exert an antiarrhythmic effect by inhibiting calcium ion channels in the myocardial cell membranes through the suppression of a slow response based on a slow inward calcium current; and other drugs such as digitalis and adenosine [Vaughan Williams, E. M., J. Clin. Pharmacol., 24, 129 (1984)].

Adenosine 5'-triphosphate (ATP), like adenosine, is known to possess the antiarrhythmic activity [Somlo, E., Lancet, 268, 1125 (1955); and Komor, K. and Garas, Z., Lancet, 269, 93 (1955)] and has now attracted attention owing to its potential as a new drug for treating arrhythmia. Such application of ATP is known to impart the following advantages: successful arrest of the paroxysmal supraventricular tachycardia; shorter time required for onset of the clinical effect of ATP, successively increasable dosage, and efficacy against the paroxysmal supraventricular tachycardia which is insusceptible to other antiarrhythmic drugs such as verapamil, digoxin and ajimaline [Otsuka, F., Kagoshima, T. and Ishikawa, H., Yakkyoku, 37(4), 25-28 (1986)].

Other heart diseases, for example, coronary atherosclerosis, myocardial infarction and angina pectoris, have been reported to arise from a diminished coronary blood flow. The coronary blood flow is affected by direct actions on coronary vessels of coronary vasomodulators such as adenosine, prostaglandins, cyclic AMP, noradrenaline, adrenaline and acetylcholine, or by indirect actions via variations of myocardial contractility, heart rate and blood pressure.

Therefore, the following coronary vasodilators which increase the coronary blood flow by dilating the coronary vessels are conventionally known: nitrites, substances for enhancing the activity of adenosine, calcium antagonists and phosphodiesterase inhibitors [Nakagawa, Y., Yakkyoku, 40(1), 245-253 (1989)]. Among them, the substances for enhancing the activity of adenosine which is considered to be a modulator of the coronary circulation give rise to a dilatation of coronary vessels and/or a formation of collateral vessels by enhancing its activity [Berne, R. M., Circ. Res., 47, 807-813 (1980)].

ATP has been reported to show some pharmacological effects, for example, vasodilation [Fujii, M. and Nakamura, M., Jap. Heart J., 18, 132 (1977)], enhancement of in vivo metabolic activity, increase in muscle contraction, and rise of efficiency of the neural transmission, as well as the aforementioned antiarrhythmic effect. As described below, however, the inventors found that ATP itself has platelet-aggregating activity. ATP may eventually bring the risk of increasing a blood viscosity, thereby causing a disturbance in the myocardial microcirculation. Accordingly, the use of ATP as a drug for treatment of heart diseases would be unadvisable and rather should be restricted in view of the above disturbance.

One object of the present invention is to provide a highly potent pharmaceutical composition for treating a heart disease, which is capable of replacing ATP and which is endowed with coronary vasodilative activity and antiplatelet activity as well as ATP-like antiarrhythmic activity.

Another object of the present invention is to provide a method for treating a subject having a heart disease which comprises administering said pharmaceutical composition to the subject.

SUMMARY OF THE INVENTION

The present invention provides a pharmaceutical composition for treating a heart disease which comprises a therapeutically effective amount of diadenosine 5',5'''-P$^1$, P$^4$-tetraphosphate, hereinafter referred to as "Ap$_4$A", as an active ingredient in admixture with a pharmaceutically acceptable carrier or diluent. The composition is particularly characterized by having antiarrhythmic and coronary vasodilative activities.

The present invention also provides a method for treating a subject having a heart disease or particularly arrhythmia, which comprises administering to the subject an effective amount of said pharmaceutical composition.

BRIEF DESCRIPTION OF THE DRAWINGS

FIG. 5 shows a comparison of the effect of Ap4A with that of ATP on ADP-induced platelet aggregation.

DETAILED DESCRIPTION OF THE INVENTION

Ap4A is a novel type of nucleotide discovered in human platelets in a recent year and has the following chemical structure:

The active ingredient Ap4A of the pharmaceutical composition according to the present invention is thus preferably in a form of a pharmaceutically acceptable salt thereof such as sodium salt, or it may be in a form of free acid thereof. Ap4A can be produced by a conventional organic synthesis or by an enzymatic synthesis with, for example, leucyl tRNA synthetase derived from thermophilic Bacillus stearothermoohillus (Japanese Patent Application Laid-Open (KOKAI) No. 62-278992; U.S. Pat. NO. 4886749; EP-A-247819), using ATP as the starting material in either method. The half lethal dose ($LD_{50}$) of Ap4A was found to be 102 mg/kg (rat; i.v.) as determined by the Lichfield-Wilcoxon method. As to the biological activities of Ap4A, there are the following reports: inhibitory effect on the adenosine diphosphate (ADP)-stimulated human platelet aggregation [Luthje, J. and Ogiluie, A., Biochem. Biophys. Res. Commun., 118, 704–709 (1984)], enhancement of DNA synthesis in baby hamster kidney cells [Grummt, F., Proc. Natl. Acad. Sci. U.S.A. 75 371-375 (1978)], promotion of the growth of hepatocytes [Rapaport, L. and Zamecnick, P. C., Proc. Natl. Acad. Sci. U.S.A., 73 3984-3988 (1976)], and vasodilative action on the rabbit mesenteric artery [Busse, R., Ogiluie, A. and Pohl, U., Am. J. Physiol., 254, 828-832 (1988)].

However, there have been no reports on the antiarrhythmic and coronary vasodilative activities of Ap4A, and the use of Ap4A as an drug for treating a heart disease is not known at all. The present inventor's have now found that Ap4A possesses antiarrhythmic and coronary vasodilative activities The present invention provides a pharmaceutical composition for treating a heart disease which comprises a therapeutically effective amount of diadenosine 5',5'''-$P^1$,$P^4$-tetraphosphate as an active ingredient in admixture with a pharmaceutically acceptable carrier or diluent.

The pharmaceutical composition of the present invention contains Ap4A as an active ingredient. Ap4A has the antiarrhythmic activity virtually equivalent to that of ATP, the coronary vasodilatative activity and the antiplatelet activity, while Ap4A itself has no activity of platelet aggregation even at a concentration of $3 \times 10^{-4}$M, as illustrated below. Therefore, Ap4A is effective in the treatment of heart diseases such as arrhythmia, angina pectoris, coronary atherosclerosis and myocardial infarction, preferably of arrhythmia, and of a complication thereof. Because Ap4A also has a prophylactic effect against thrombosis via its anti-platelet activity, in addition to the above specific activities, it is highly useful as a drug for treatment of heart diseases.

Figure 1:
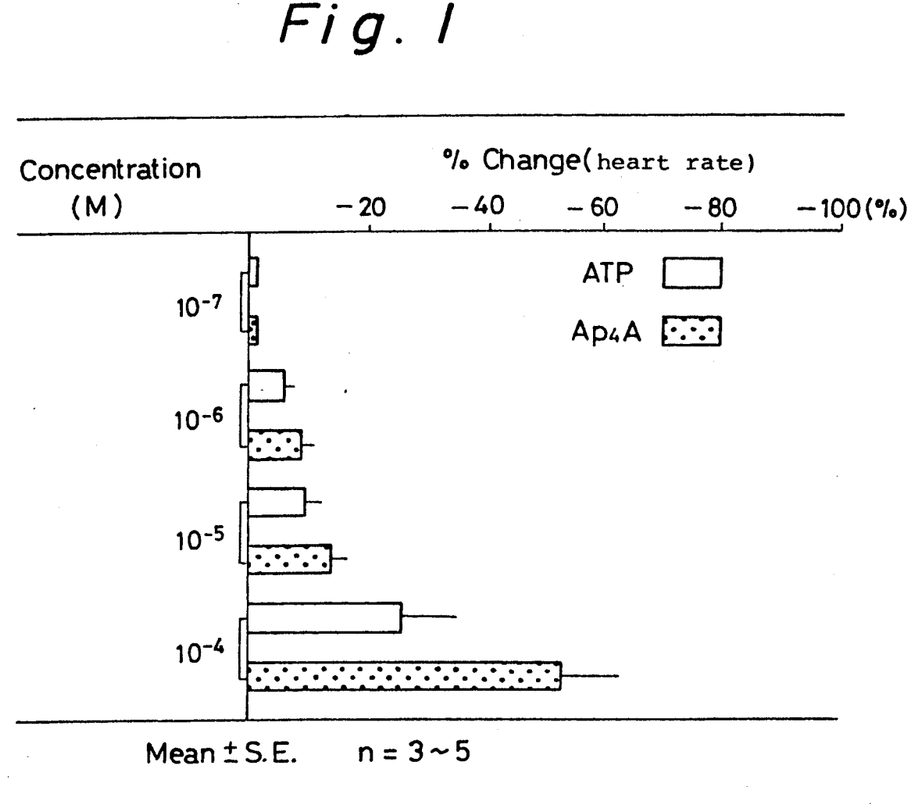
FIG. 1 shows a negative inotropic effect of Ap$_4$A on an isolated guinea pig right atrium.

FIG. 1 shows the negative inotropic effect of Ap4A as observed in the right atrium which was taken out from a guinea pig and exposed to Ap4A of different concentrations, together with the results observed with ATP for comparison. The measurements of response to a single dose of the drug indicated that Ap4A reduced the heart rate with a dose-dependency as the case of ATP and consequently showed a bradycardic effect. Such an effect of Ap4A was maintained until Ap4A was removed from Ap4A-acting system, though varying with a concentration of the drug (data not shown). It was also noted that Ap4A was prone to be more potent than ATP, when compared in terms of the percent change of heart rate.

Figure 2:
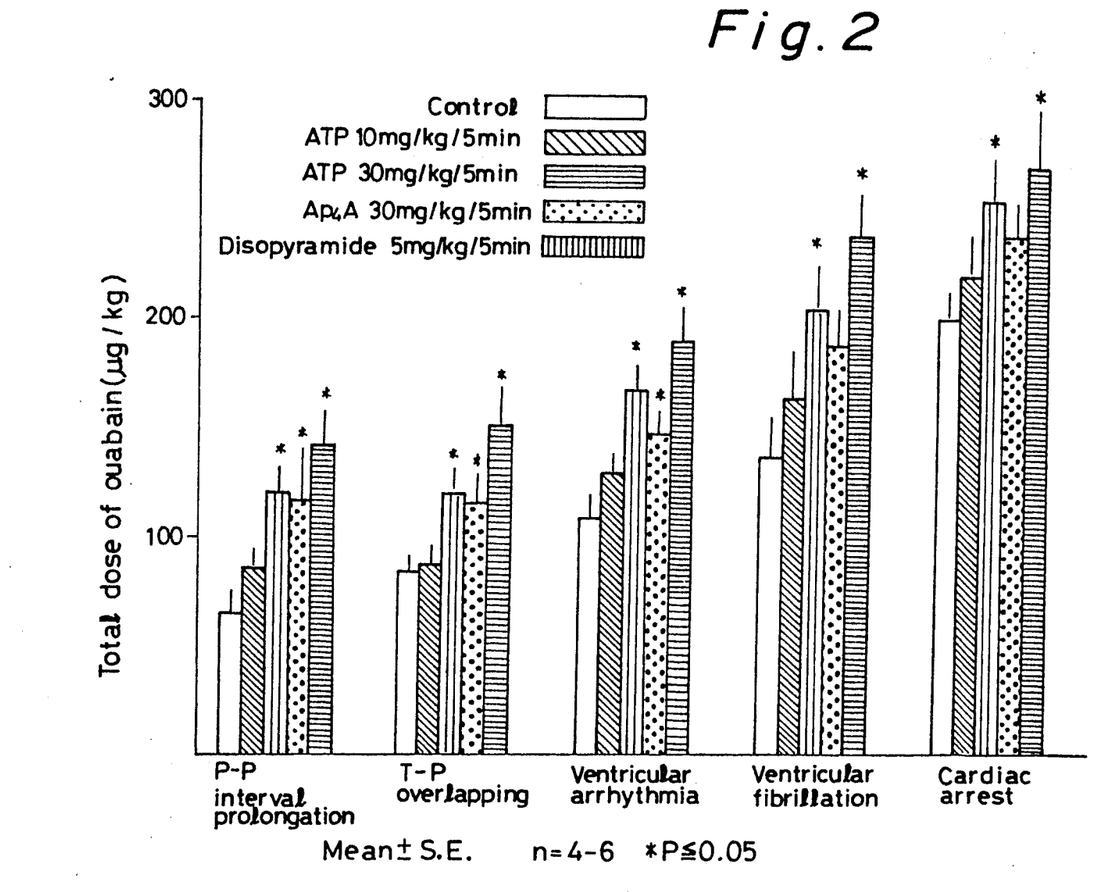
FIG. 2 shows an antiarrhythmic effect of Ap4A on a model of ouabain-induced cardiac arrhythmia.

FIG. 2 illustrates the antiarrhythmic effect of Ap4A on an ouabain-induced arrhthymia model in comparison with the effects of ATP and disopyramide. It was found that Ap4A has an antiarrhythmic activity as do ATP and disopyramide, as seen from the results that Ap4A inhibited the onsets of such parameters as P-P interval prolongation, T-P overlapping, ventricular arrhythmia, ventricular fibrillation and cardiac arrest. The antiarrhythmic activity of Ap4A was practically the same as that of ATP, or slightly lower, when compared at the same concentration.

Figure 3:
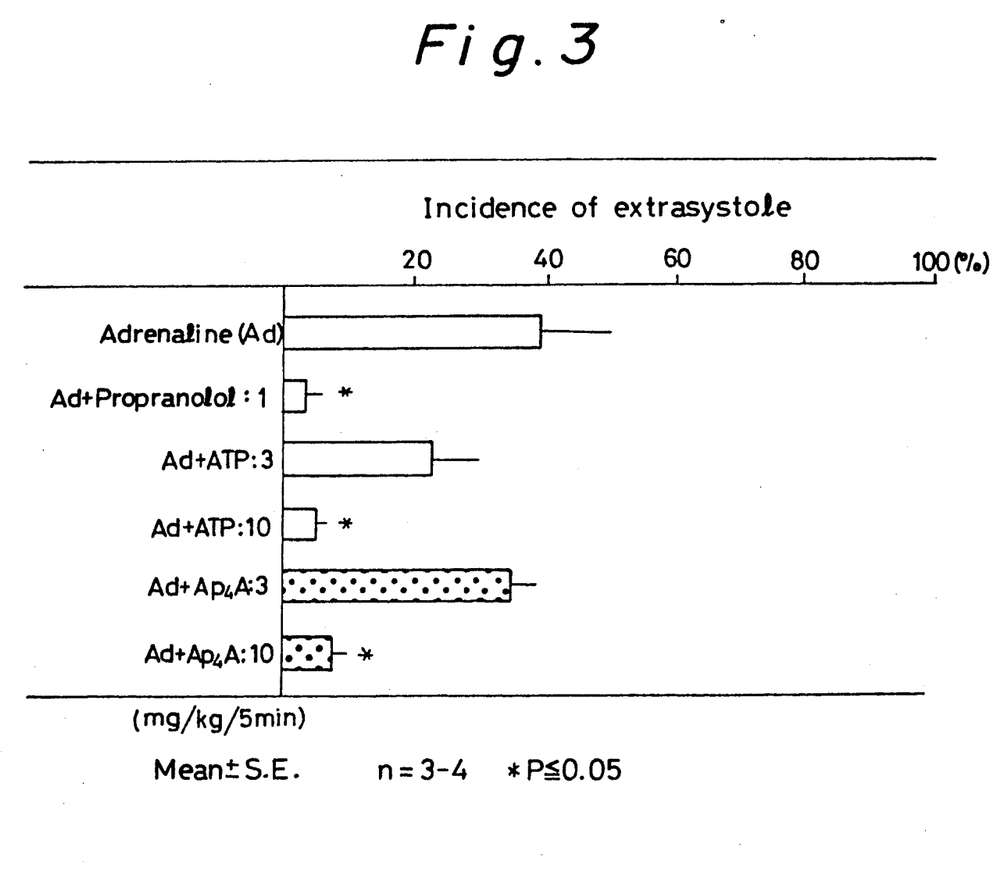
FIG. 3 shows an antiarrhythmic effect of Ap4A on a model of adrenaline-induced cardiac arrhythmia.

The antiarrhythmic effect of Ap4A on an adrenaline-induced arrhythmia model is compared with that of ATP or propranolol in FIG. 3. When the grading of arrhythmia was assessed in terms of the incidence of extrasystole, Ap4A reduced the incidence of extrasystole with a dose-dependency as did ATP and propranolol. Accordingly, this is an evidence to corroborate the antiarrhythmic effect of Ap4A. The effect of Ap4A was somewhat inferior to that of ATP.

Thus, the antiarrhythmic activity of Ap4A was verified in the two types of cardiac arrhythmia models induced with ouabain and adrenalin, and it was found that the antiarrhythmic efficacy of Ap4A is analogous to ATP. From the two experiments on these models, it is inferred that the antiarrhythmic effect of Ap$_4$A is exerted probably via its ability to produce a bradycardic response by inhibiting the sinoatrial node, which mechanism is also the case of ATP.

Figure 4:
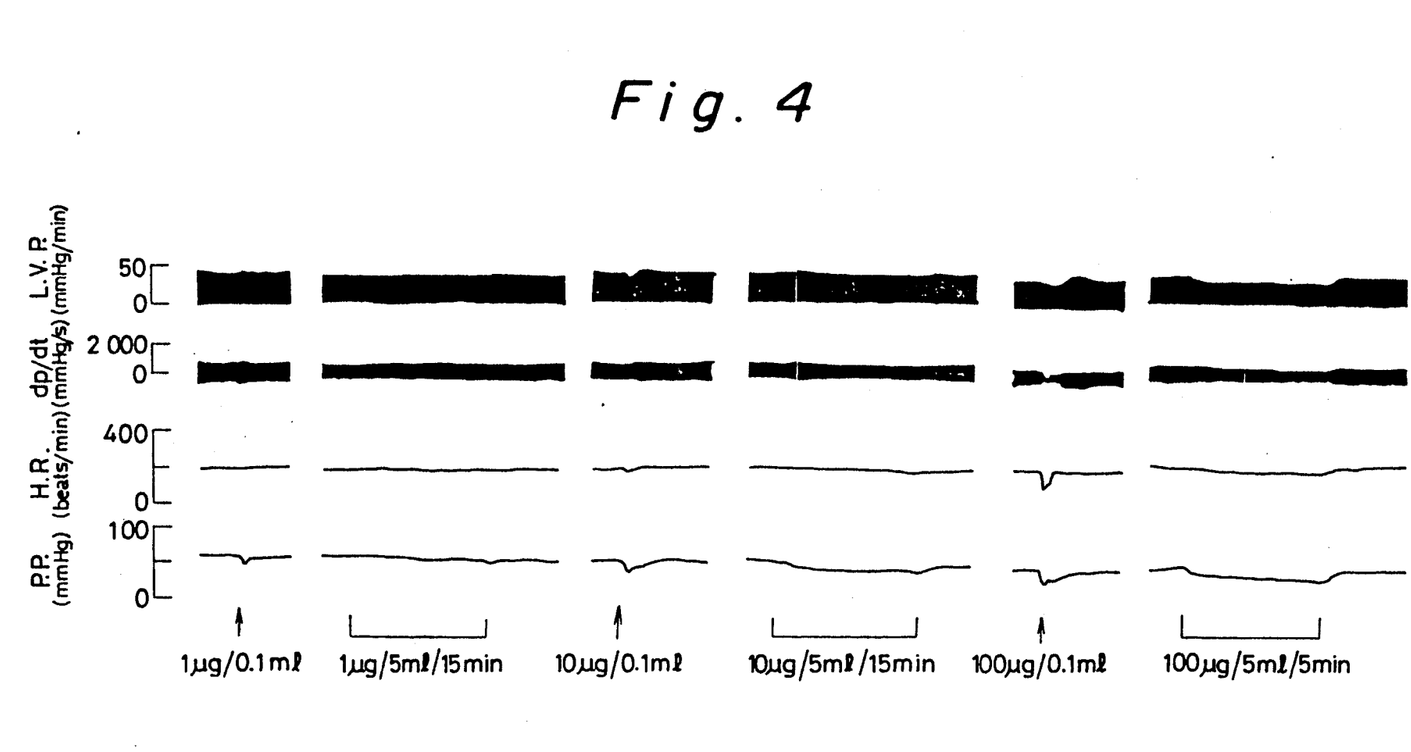
FIG. 4 shows antiarrhythmic and coronary vasodilative activities of Ap4A, wherein the abbreviations used are P. P., perfusion pressure; H. R., heart rate; dP/dT, differential value of left ventricular pressure; L. V. P., left ventricular pressure.

FIG. 4 shows a change of perfusion pressure observed when the guinea pig heart was removed and placed under Langendorff perfusion and Ap$_4$A was then added to the perfusion system in a single or continuous dose. In either method of the administration of Ap$_4$A, the perfusion pressure decreased depending on the dose. This finding indicates that Ap$_4$A possesses coronary vasodilative activity other than antiarrhythmic activity. The coronary vasodilative effect was demonstratable at the dose which did not affect the heart rate or left ventricular pressure, e.g., 1 μg. Thus, Ap$_4$A is expected to be a highly potent coronary vasodilative agent.

In FIG. 5, an inhibitory effect of Ap$_4$A on ADP-induced platelet aggregation is compared with that of ATP. ATP which was administered at a concentration of $3 \times 10^{-5}$M or more in the absence of ADP caused a dose-dependent aggregation of platelets, while Ap$_4$A did not cause platelet aggregation at all under the same conditions. When Ap$_4$A was added to the platelet-rich plasma derived from a rabbit at a concentration of, for example, from $3 \times 10^{-5}$M to $3 \times 10^{-4}$M, prior to an addition of ADP (5 μM), Ap$_4$A markedly inhibited ADP-induced platelet aggregation with a dose-dependency, as described by J. Luthje and A. Ogiluie (see the above cited reference). For example, Ap$_4$A at $3 \times 10^{-4}$M inhibited the platelet aggregation by 76%.

As stated hereinabove, Ap$_4$A has antiarrhythmic activity analogous to ATP and at the same time is endowed with the activities of coronary vasodilation and antiplatelet aggregation. Therefore, the pharmaceutical composition of the present invention will avoid the problem of a disturbance of myocardial microcirculation caused by the platelet aggregation inherent in ATP itself.

The present invention further provides a method for treating a subject having a heart disease which comprises administering to the subject an effective amount of the pharmaceutical composition described above.

The present invention also provides a method for treating a subject having arrhythmia which comprises administering to the subject an effective amount of said pharmaceutical composition.

The pharmaceutical composition of the present invention may be applied by oral administration or by injection, e.g., intravenously and intramuscularly. The pharmaceutical composition of the present invention may be administered at an effective dosage level of Ap$_4$A of, for example, 10–2000 mg/day/adult orally or 1–500 mg/day/adult intravenously. A patient with a heart disease may be administered orally in divided doses intravenously or by a slow infusion over a certain length of time. The dosage and method of administration may be individualized according to patient's age, symptom, body weight, etc.

In the pharmaceutical composition of the present invention, a therapeutically effective amount of Ap$_4$A is combined with an inert carrier or diluent. Conventional carriers or diluents may be used and the pharmaceutical composition of the present invention may further contain one or more pharmaceutically acceptable additives such as preservatives, stabilizers and perfumes. The pharmaceutical composition of the invention may be prepared in the form of granules, tablet, capsule, injection, parenteral infusion fluid, or the like, and its form is generally selected according to patient's age, symptom and other factors.

The present invention will be further illustrated by the following examples.

EXAMPLE 1

(A) Effect of Ap$_4$A on guinea pug right atrium

A guinea pig (b.w. 450 g) was stunned and was immediately removed its heart to excise the right atrium therefrom. The right atrium was then suspended in a Magnus tube (30 ml) filled with Krebs-Henseleit (KH) solution which was maintained at 31° C. constantly aerating with a mixture of 95% $O_2$—5% $CO_2$ therein. After the KH solution was changed with the fresh one at 15-minutes intervals and the heart rate of the right atrium was stabilized in 60–90 minutes, Ap$_4$A or ATP which was prepared at different concentrations was added to the KH solution in a single dose to determine the change of heart rate. Drug concentrations of $10^{-4}$, $10^{-5}$, $10^{-6}$ and $10^{-7}$M were employed in this experiment. The heart rate was determined with a cardiotachometer (Nihon Kohden Co.; Model AT601G; Japan) and an isometric converter (Nihon Kohden Co.; Model TB-651T), with a 1-g weight load. Results are shown in FIG. 1.

As seen in FIG. 1, both Ap$_4$A and ATP decreased the atrial heart rate with a dose-dependency, and this means that these drugs have a bradycardic effect. When their changes of heart rate are compared, the potency of Ap$_4$A tends to be greater than that of ATP; the relative potency of Ap$_4$A was 1.5-fold at $10^{-6}$M, 1.5-fold at $10^{-5}$M and 2.1-fold at $10^{-4}$M.

(B) Effect of Ap$_4$A on ouabain-induced arrhythmia

With a guinea pig (b.w. 450 g) placed under urethane anesthesia (1.1 g/kg), its femoral vein, jugular vein and carotid artery were cannulated. Ap$_4$A, ATP or disopyramide was injected into the femoral vein and ouabain into the jugular vein through each cannula, while the carotid artery was utilized for a blood pressure monitoring. Changes associated with the administration of the drug were assessed by monitoring electrocardiogram (ECG), blood pressure, mean blood pressure and heart rate (Nihon Kohden Co.; Models AB620G, AP601G and AT601G). ECG was recorded in accordance with the lead II.

Ouabain-induced cardiac arrhythmia model was prepared by continuous infusion of ouabain at a rate of 7 μg/kg/min via the jugular vein. Each drug was administered by intravenous infusion over a period of 5 minutes at the following dose: ATP, 10 or 30 mg/kg; Ap$_4$A, 30 mg/kg; and disopyramide, 5 mg/kg. The drug was administered simultaneously with the infusion of ouabain. The antiarrhythmic effect of the drug tested was assessed in terms of the total dose of ouabain given until onset of each of the following parameters: P-P interval prolongation, T-P overlapping, ventricular arrhythmia, ventricular fibrillation and cardiac arrest. Results are shown in FIG. 2.

The data indicated a marked antiarrhythmic effect of Ap$_4$A which inhibited all these parameters as did ATP and disopyramide. The antiarrhythmic effect of Ap$_4$A at a dose of 30 mg/kg was virtually comparable with or slightly inferior to that of ATP at the same dose.

(C) Effect of Ap4A on adrenaline-induced arrhythmia

With a guinea pig (b.w. 450 g) placed under urethane anesthesia (1.1 g/kg), its femoral vein, jugular vein and carotid artery were cannulated. Ap4A, ATP or propranolol was injected into the femoral vein and adrenaline into the jugular vein through each cannula, while the carotid artery was utilized for a blood pressure monitoring. Changes associated with the administration of the drug were monitored in the same manner as above (B), and ECG was recorded in accordance with the lead II.

Adrenaline-induced cardiac arrhythmia model was prepared by injecting adrenaline (10 μg/kg) into the jugular vein over 5 seconds. Each drug was administered by intravenous infusion over a period of 5 minutes at the following dose: ATP, 3 or 10 mg/kg; Ap4A, 3 or 10 mg/kg; propranolol, 1 mg/kg. Adrenaline was administered in a single dose 4 minutes after administration of the drug tested. The grading of arrhythmia was assessed in terms of the incidence of extrasystole. Results are shown in FIG. 3.

Ap4A exhibited an antiarrhythmic effect with a dose-dependent reduction of the incidence of extrasystole, as did ATP and propranolol. The effect of Ap4A was somewhat weaker than that of ATP. For example, the incidence of extrasystole at a dose of 10 mg/kg/5min was 5.3% with ATP and 8.0% with Ap4A, as compared to a control value of 39%.

EXAMPLE 2

Coronary vasodilative effect

An experiment was performed by a modification of the method of Aronson and Serlick [Toxicol. Appl. Pharmac., 38, 479–488 (1976) and 39, 157–176 (1977); Biochem. Pharmac. 26, 2297–2305 (1977)]. The guinea pig heart removed was started perfusing at the origin of the aorta by the Langendorff perfusion method. Perfusion was carried out at 37° C. and 14 ml/min of flow rate with a peristalic pump (TAIYO TYPE 1500N; Japan) in Krebs-Henseleit solution (KH: NaCl, 118 mM; phosphate, 1.2 mM; $NaHCO_3$, 25 mM; glucose, 10 mM; KCl, 4.7 mM; $CaCl_2$, 2.5 mM; and $MgSO_4$, 1.2 mM; pH 7.4; bubbling with 95% $O_2$- 5% $CO_2$). After the initiation of the perfusion, an incision was made in the left auricle and a cannula was inserted into the left ventricle via the left atrium to measure the left ventricular pressure with a pressure transducer (Nihon Kohden Co.; Model TP-200T). The differential value of the left ventricular pressure (dp/dt) was measured with a cardiotachometer (Nihon Kohden Co.; Model AT-601G). The perfusion pressure was determined with a pressure transducer connected to the aortic cannula. Ap4A was dissolved in KH at various concentrations and administered to the perfusion system in a single dose of 1–100 μg/0.1 ml/5 sec or by a continuous infusion of 1–100 μg/5ml/15 min. Results are shown in FIG. 4.

The data indicated a dose-dependent fall of perfusion pressure and a marked decrease of heart rate after the single dose of Ap4A. In addition, the left ventricular pressure fell transiently after administration and subsequently it was elevated. The effect of Ap4A on the perfusion pressure was observed from the lowest dose of Ap4A. In the continuous infusion of Ap4A, the perfusion pressure and the left ventricular pressure decreased depending on the dose of Ap4A. The decrease of perfusion pressure clearly indicates that Ap4A has coronary vasodilative activity.

EXAMPLE 3

Effect of Ap4A on ADP-induced platelet aggregation

Figure 5A:
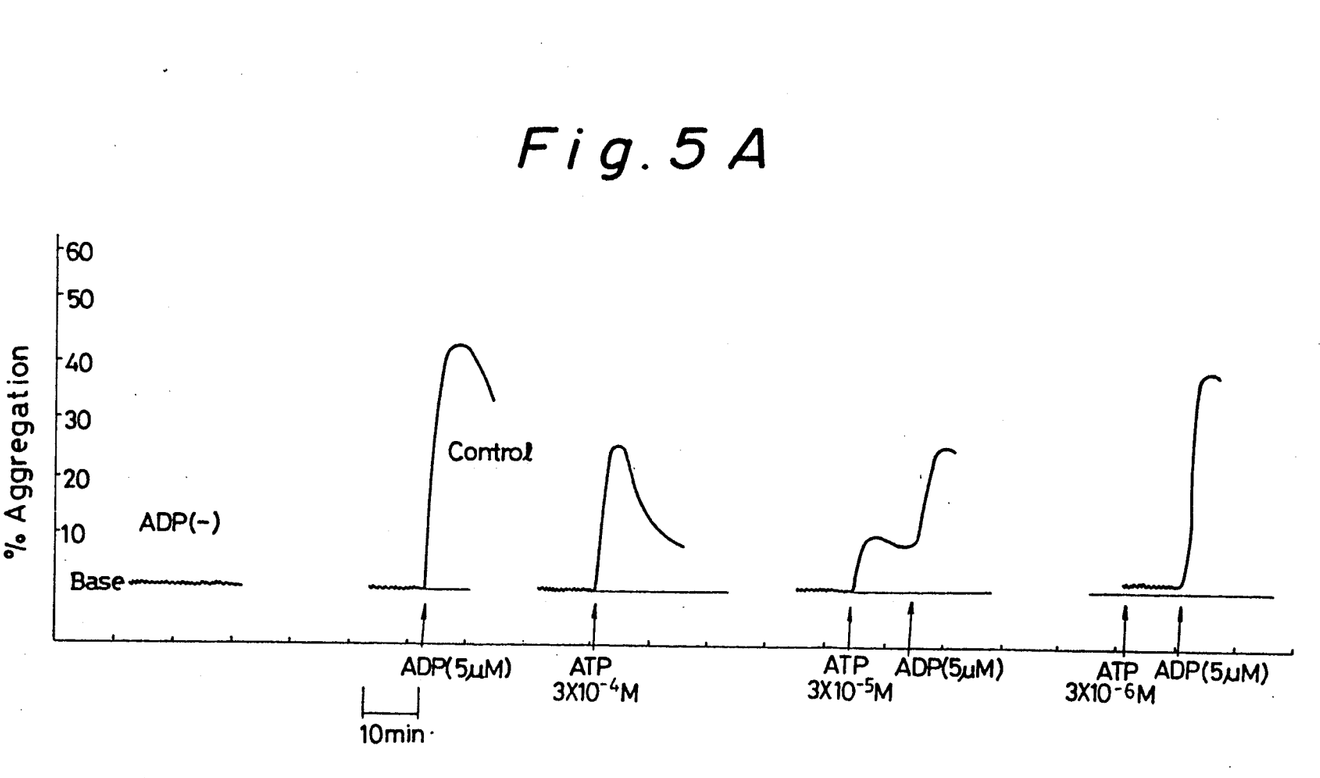
FIG. 5A depicts the effect of ATP and FIG. 5B the effect of Ap4A.

Blood was collected from the carotid artery of an unanesthetized rabbit into a syringe containing one volume of 3.8% sodium citrate per nine volumes of blood. The citrated blood was centrifuged at 1100 rpm for 15 minutes, and the supernatant was obtained as platelet-rich plasma (PRP). To 200 μl of PRP in an aggregometer, 10 μl of ATP or Ap4A solution was added and the mixture was incubated at 37° C. for 10 minutes, followed by addition of 10 μl of 0.1 mM ADP solution (final concentration: 5μM) to induce and measure the aggregation of platelets. Results obtained for ATP are shown in FIG. 5A and those for Ap4A in FIG. 5B.

Figure 5B:
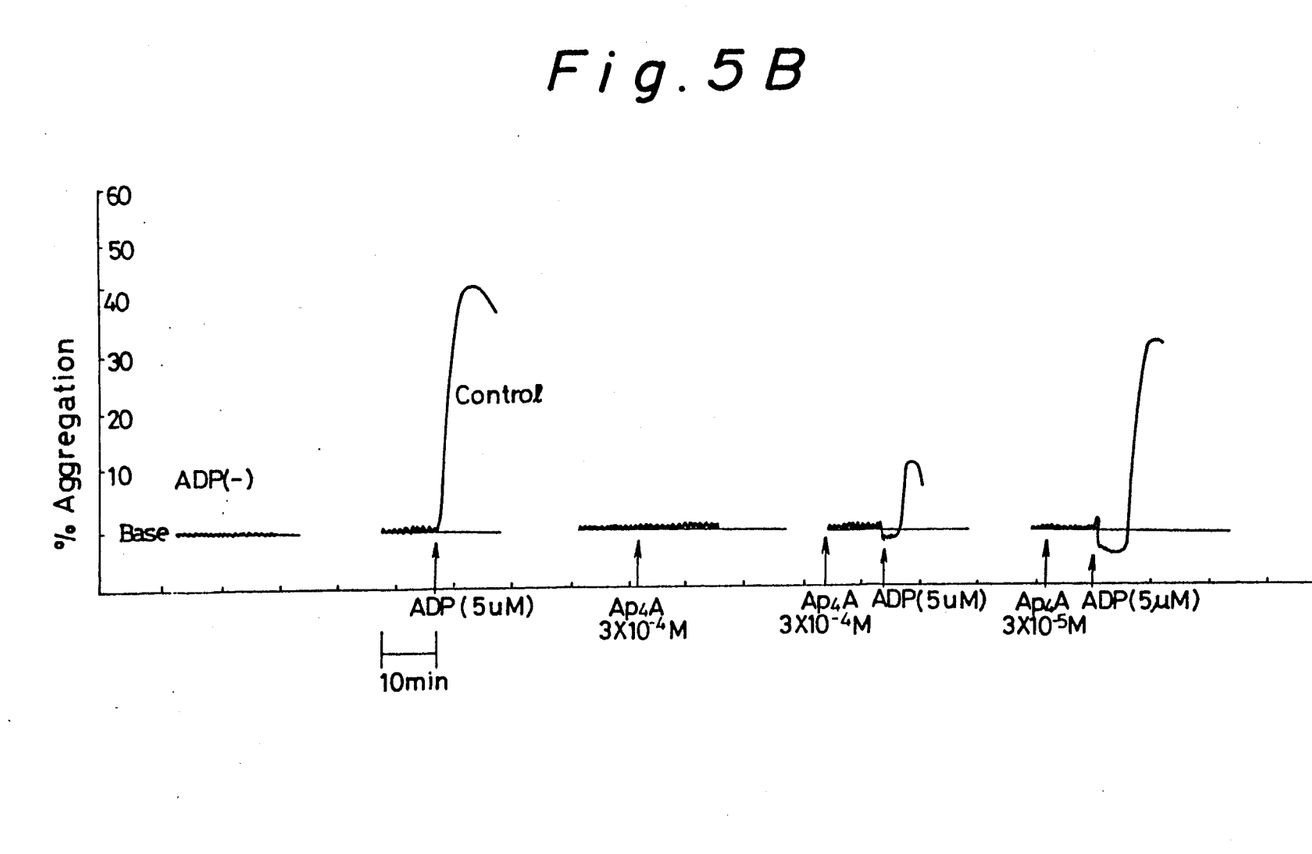

As seen in FIG. 5B, ADP-induced platelet aggregation was inhibited by Ap4A with a dose-dependency, namely, by 76% at $3 \times 10^{-4}M$ and 21% at $3 \times 10^{-5}M$, as compared to the control. In addition, Ap4A itself had no effect of the platelet aggregation even at a concentration of $3 \times 10^{-4}M$. ATP caused a dose-dependent aggregation of platelets at concentrations of $3 \times 10^{-5}M$ or more (FIG. 5A).

What is claimed is:

1. A method for treating a mammal having arrhythmia, which comprises administering to the mammal a therapeutically effective amount of diadenosine 5′, 5′′′-$P^{-1}$, $P^{-4}$-tetraphosphate or a pharmaceutically acceptable salt thereof as an active ingredient in admixture with a pharmaceutically acceptable carrier or diluent.

2. The method according to claim 1 wherein the therapeutically effective amount ranges between 10 and 2000 mg/day/adult when administering orally or between 1 and 500 mg/day/adult when administered intravenously.

3. The method according to claim 1 wherein the mammal is a human.

4. The method according to claim 2 wherein the mammal is a human.